US012593960B2

(12) United States Patent
Hallauer et al.

(10) Patent No.: US 12,593,960 B2
(45) Date of Patent: Apr. 7, 2026

(54) ENDOSCOPE PROVIDED WITH A DEVICE FOR CLOSING A FLUID FLOW CIRCUIT, FOR IMPROVED STERILISATION

(71) Applicant: AXESS VISION TECHNOLOGY, Joue-les-Tours (FR)

(72) Inventors: Emmanuel Hallauer, Sache (FR); Philippe Le Roux, Tours (FR)

(73) Assignee: AXESS VISION TECH, Joue-les-Tours (FR)

( * ) Notice: Subject to any disclaimer, the term of this patent is extended or adjusted under 35 U.S.C. 154(b) by 452 days.

(21) Appl. No.: 17/793,070

(22) PCT Filed: Dec. 22, 2020

(86) PCT No.: PCT/FR2020/052592
§ 371 (c)(1),
(2) Date: Jul. 15, 2022

(87) PCT Pub. No.: WO2021/144512
PCT Pub. Date: Jul. 22, 2021

(65) Prior Publication Data
US 2023/0038305 A1     Feb. 9, 2023

(30) Foreign Application Priority Data

Jan. 17, 2020    (FR) ...................................... 2000445

(51) Int. Cl.
*A61B 1/00*          (2006.01)
*A61B 1/015*         (2006.01)
(52) U.S. Cl.
CPC ........ *A61B 1/00068* (2013.01); *A61B 1/0014* (2013.01); *A61B 1/015* (2013.01)
(58) Field of Classification Search
CPC .... A61B 1/00068; A61B 1/0014; A61B 1/015
See application file for complete search history.

(56)                References Cited

U.S. PATENT DOCUMENTS 6,017,322  A      1/2000  Snoke et al.
8,182,419  B2     5/2012  Kohno et al.
                    (Continued)

FOREIGN PATENT DOCUMENTS

DE        102014201208 A1     7/2015
EP            0055394 A1  *  7/1982    ......... A61B 1/00068
                    (Continued)

OTHER PUBLICATIONS

English Abstract of FR2955242.

*Primary Examiner* — Michael J Carey
*Assistant Examiner* — Megan Elizabeth Monahan
(74) *Attorney, Agent, or Firm* — Oliff PLC

(57)                ABSTRACT

The disclosure relates to a medical endoscope including:
  a piston body in which a piston is movably mounted in displacement;
  the piston delimiting with the piston body a sealed obturation section and a sealed interconnection chamber adapted so that, in the open position of the obturation device, the sealed interconnection chamber ensures communication between a first portion and a second portion of the circulation circuit. According to the disclosure, the sealed interconnection chamber including a hole passing right through the piston to open out into a cylindrical chamber delimited between the piston and the piston body, by an oblong section located in the open position of the circulation circuit, facing the inlet sections of the tubing for connection to the first portion and to the second portion of the circulation circuit to limit the pressure drop.

11 Claims, 4 Drawing Sheets

(56)          References Cited

U.S. PATENT DOCUMENTS

2005/0119527 A1 *   6/2005   Banik ................ A61B 1/00066
                                                    600/117
2011/0233439 A1 *   9/2011   Lee .................... A61B 1/00068
                                                    251/319
2011/0251460 A1    10/2011   Jiang et al.
2016/0338577 A1    11/2016   Viebach et al.
2020/0093360 A1 *   3/2020   Chu ................... A61B 1/00101

FOREIGN PATENT DOCUMENTS

EP          0071058  A1      2/1983
EP          0075275  A1      3/1983
EP          0120454  A1     10/1984
EP          0055394       *  3/1985   .............. A61B 1/12
FR          2955242  A1      7/2011

* cited by examiner

[Fig. 1]
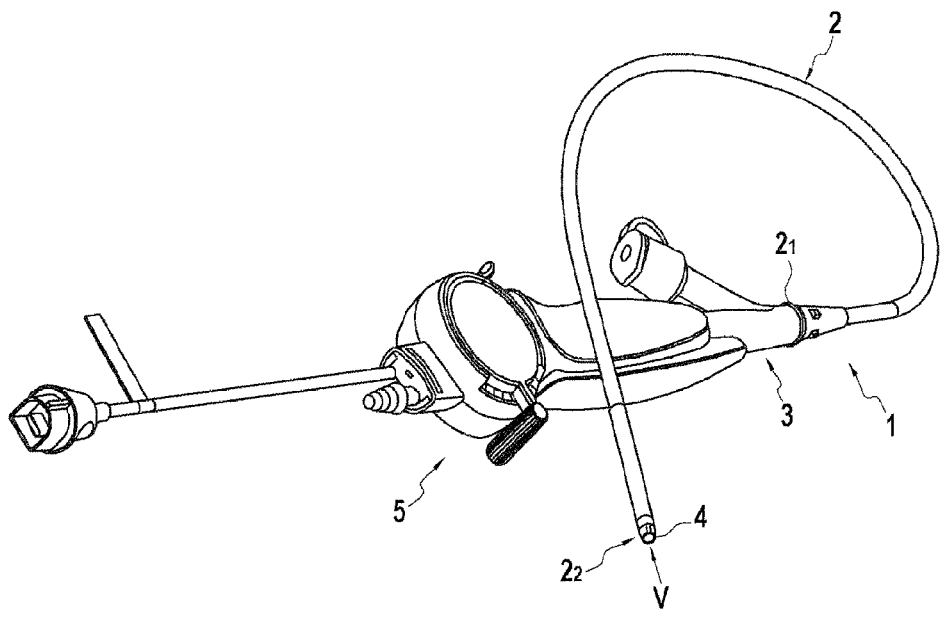
[Fig. 2]
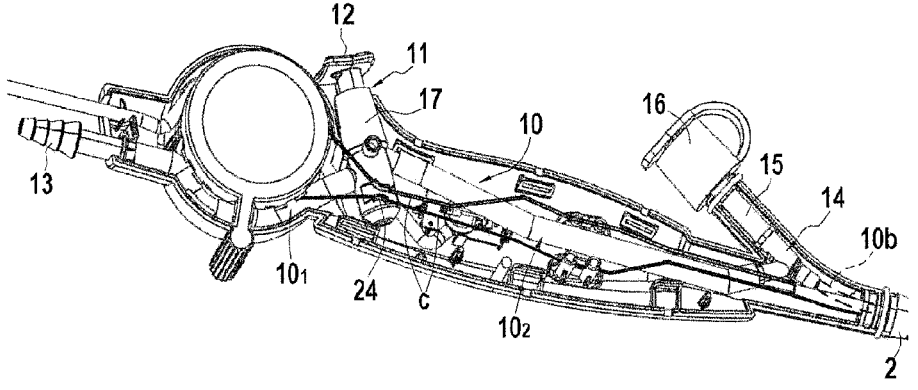

[Fig. 3]
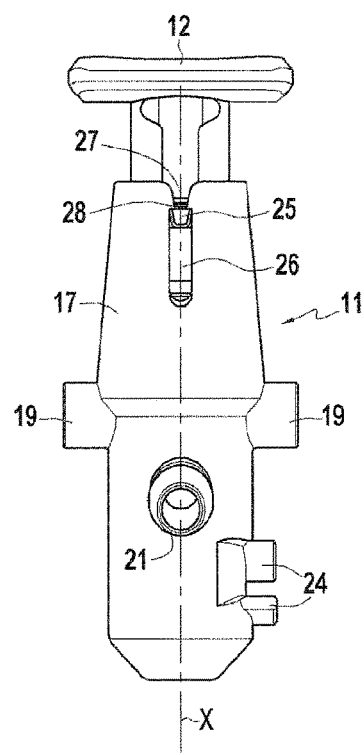
[Fig. 4]
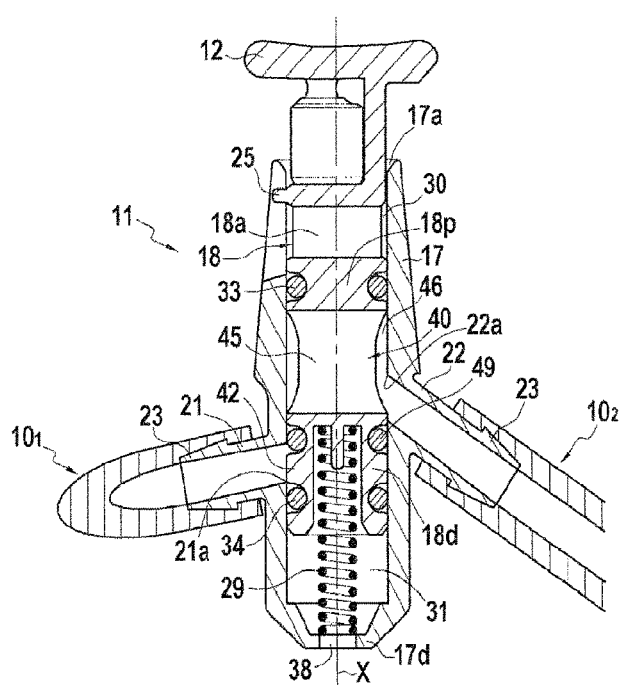

[Fig. 5]
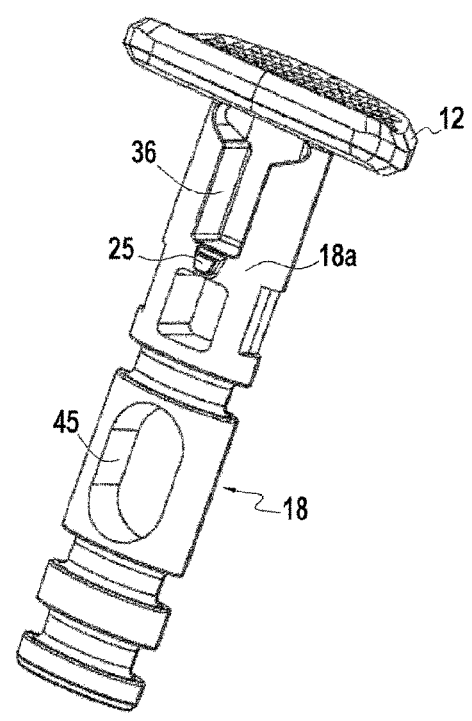
[Fig. 6]
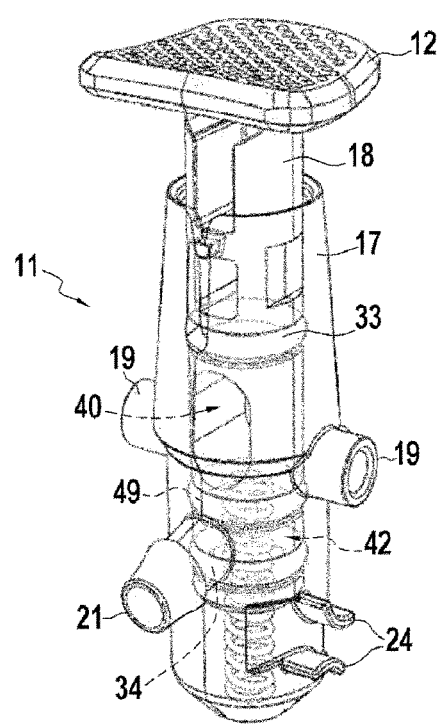

[Fig. 7]
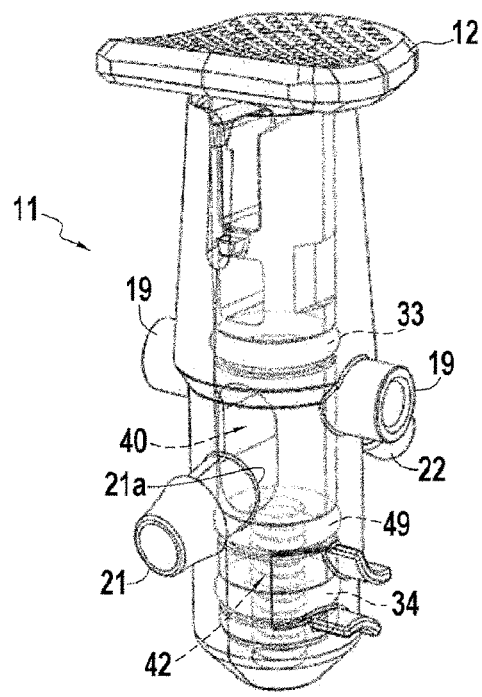
[Fig. 8]
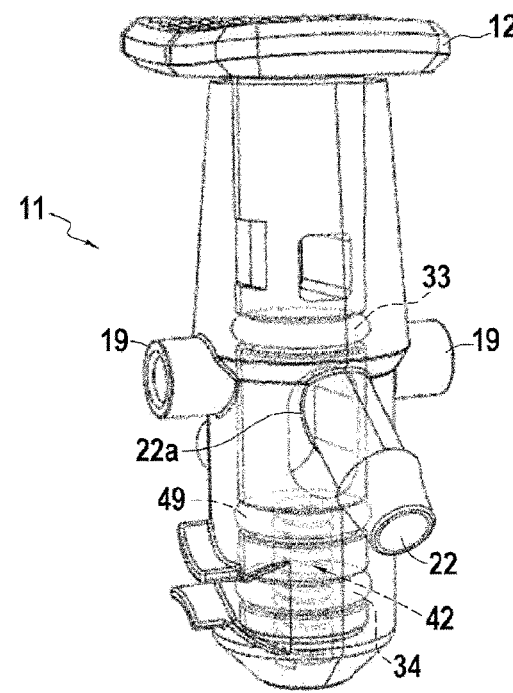

ENDOSCOPE PROVIDED WITH A DEVICE FOR CLOSING A FLUID FLOW CIRCUIT, FOR IMPROVED STERILISATION

TECHNICAL FIELD

The present disclosure relates to the technical field of medical endoscopes in a general sense for accessing the interior of a hollow organ, a cavity or a natural or artificial conduit of the human body with a view to performing various operations for therapeutic, surgical or diagnostic purposes.

The object of the disclosure more specifically relates to an endoscope equipped with a circuit for circulating a fluid whose flow rate is to be monitored, such a circuit ensuring in particular either the injection of a fluid, for example an irrigation fluid for washing or irrigating the tissues or the aspiration of the injected irrigation fluid or of body fluids associated or not with tissue debris.

The object of the disclosure relates more specifically but not exclusively to a single-use medical endoscope.

The endoscope according to the disclosure is used for diagnostic, therapeutic or surgical purposes for the inspection of all inner parts of the human body accessible by the natural or artificial paths. For example, the endoscope according to the disclosure can be used in the field of urinary tract, gastrointestinal tract, respiratory system, cardiovascular system, trachea, sinus cavity, women's reproductive system, abdominal cavity or any other part of the human body to be explored by a natural or artificial path.

BACKGROUND

In the state of the art, various solutions for making an endoscope are known, including a fluid circulation circuit. For example, U.S. Pat. No. 6,017,322 describes an endoscope including a control handle to which a tubular structure is fixed including a distal head equipped with a vision system that allows illuminating and examining the organ, the cavity or the conduit of the human body. Upstream of the distal head, the tubular insertion structure includes a bending or deflection part controlled by the control handle and allows orienting the distal head inside the insertion path.

This tubular structure is adapted to allow bringing at the distal head, one or several devices designed to perform different functions such as for example the supply of instruments, the collection of samples or the conduction of surgical procedures.

This endoscope is able to be provided with equipment including one or several tubular conduits, extending along the insertion tube and provided at its proximal end with a removable mounting connector on the handle. This mounting connector is intended to be connected to a system for supplying or aspirating fluids. This solution has the advantage that the fluid circulation circuit is independent of the handle so that the handle is not soiled by the fluid emanating from the patient. However, a drawback of this endoscope relates to the difficulty in and time for mounting the tubular conduits on the handle. Furthermore, this endoscope does not integrate a technical solution for monitoring the obturation of the tubular conduits and therefore does not guarantee keeping a circuit sterile until its use.

Patent FR 2 955 242 describes an endoscope including a control handle to which a tubular structure is fixed including a distal head equipped with a vision system that allows illuminating and examining the organ, the cavity or the conduit of the human body.

Such an endoscope also includes a circulation circuit for a fluid, part of which is integrated inside the control handle. This circulation circuit is equipped with an obturation device fixed on the control handle. The obturation device includes a rod moved manually to ensure the closing of the circuit by pinching. This solution is likely to lead to a deterioration of the circuit due to its pinching and to an uncertain monitoring of the fluid flow rate necessarily leading to a pressure drop.

Patent application EP 0 055 394 describes an endoscope provided with a valve device for supplying air and water to the control section of the endoscope. Such a device includes a check valve provided in the air passage to prevent air, water or the viscous products from flowing back. The air passage is provided with a leak hole opening out at the head of the piston and which can be plugged by the operator. This leak hole communicates with the air inlet endpiece by an axial channel arranged in the body of the piston and opening out into a channel arranged transversely in the body of the piston. Such a device does not provide any solution to the problem of cleaning and pressure drop of the fluid passing therethrough.

Patent applications EP 0 120 454 and EP 0 071 058 describe an endoscope provided with an obturation device for an air circuit and a water circuit intended to be brought to the distal head of the endoscope. The obturation device includes a piston body movably mounted and in which an air leakage channel communicating with the air circuit and opening out onto the control part of the piston is arranged. The obturation device described causes a pressure drop for the fluid passing therethrough.

U.S. Pat. No. 8,182,419 describes an endoscope provided with an obturation device for an air circuit and a water circuit intended to be brought to the distal head of the endoscope. The obturation device includes a movably mounted piston body and in which an elastically urged movable rod is mounted and in which a conduit allowing, when the rod is depressed, the communication between the two parts of the air circuit, is arranged. Such a device is complex in design and does not provide any solution to the problem of pressure drop for the fluid passing therethrough.

The analysis of the state of the art leads to the observation that there is a need for an endoscope designed to simply and quickly have at least one fluid circulation circuit, whose obturation can be monitored in a safe and effective manner without causing a pressure drop during the circulation of the fluid, this endoscope and particularly the fluid circulation circuit being able to be sterilized and kept sterile until it is used.

SUMMARY

The present disclosure therefore aims to satisfy this need by proposing a new medical endoscope designed to have, simply and quickly, at least one fluid circulation circuit whose obturation can be monitored in a safe and effective manner without causing a pressure drop, this endoscope and particularly the fluid circulation circuit being able to be sterilized and kept sterile until it is used.

To achieve such an objective, the medical endoscope includes an insertion tube connected at its proximal part to a control handle and provided at its distal part with a distal head, the endoscope including at least one fluid circulation circuit in which an obturation device of the circulation circuit is mounted, including:

a piston body fixed to the control handle and in which a piston is movably mounted in displacement between a closed position of the circulation circuit and an open
position of the circulation circuit;

the piston delimiting with the piston body a sealed obtu-
ration section and a sealed interconnection chamber
adapted so that, in the open position of the obturation
device, the sealed interconnection chamber ensures
communication between a first portion of the circula-
tion circuit and a second portion of the circulation
circuit, and so that in the closed position of the obtu-
ration device, the sealed interconnection chamber com-
municates with a portion of the circulation circuit while
the sealed obturation section closes the other portion of
the circulation circuit, the piston including on the one
hand, a proximal part cooperating in a sealed manner
with the piston body and extending outside the piston
body, by a button for actuating the piston and on the
other hand, a distal part cooperating in a sealed manner
with the piston body to delimit up to the bottom of the
piston body, an expansion chamber communicating
with an outlet vent arranged in the bottom of the piston
body, the sealed proximal part of the piston delimiting
up to the proximal end of the piston body, a mounting
chamber for the head of the piston communicating with
the exterior of the body, the sealed interconnection
chamber including a hole passing right through the
piston to open out into a cylindrical chamber delimited
between the piston and the piston body, by an oblong
section located in the open position of the circulation
circuit, facing the inlet sections for connection to the
first portion and to the second portion of the circulation
circuit to limit the pressure drop.

According to one alternative embodiment, the piston is
slidably guided along a direction of translation in the piston
body.

Preferably, the piston is urged by an elastic return member
to automatically return to its closed position. For example,
the elastic return member does not urge the piston into its
closed position.

Advantageously, the proximal part of the piston is pro-
vided with a proximal seal ensuring the sealing between the
mounting chamber and the sealed interconnection chamber
or the sealed obturation section.

Preferably, the distal part of the piston is provided with a
distal seal ensuring the sealing between the expansion
chamber and the sealed obturation section or the sealed
interconnection chamber.

Preferably, the sealed obturation section of the piston is
delimited on one side by the distal or proximal seal and on
the opposite side by an intermediate seal ensuring the
sealing between the sealed interconnection chamber and the
sealed obturation section.

Advantageously, the inlet sections for connection to the
first portion and to the second portion of the circulation
circuit are delimited respectively by a first tubing and a
second tubing offset from each other along the direction of
displacement of the piston.

According to one preferred exemplary embodiment, the
piston body is equipped with a first tubing for connection to
the first portion of the circulation circuit and with a second
tubing for connection to the second portion of the circulation
circuit, the first tubing and the second tubing extending on
either side of the piston body along a common plane.

Advantageously, the first tubing and the second tubing are
externally provided with an anchoring system for the por-
tions of the circulation circuit.

To facilitate its mounting, the piston body is provided
with an interlocking fixing system inside the control handle.

In addition, the piston body is externally equipped with
fins for guiding actuation cables to orient the distal head.

Various other characteristics emerge from the description
given below with reference to the appended drawings which
show, by way of non-limiting examples, embodiments of the
object of the disclosure.

BRIEF DESCRIPTION OF THE DRAWINGS

FIG. 1 is a perspective view of a medical endoscope in
accordance with the disclosure.

FIG. 2 is a partly cut-away perspective view of the control
handle of a medical endoscope in accordance with the
disclosure equipped with a fluid circulation circuit.

FIG. 3 is a perspective view showing the obturation
device of the fluid circulation circuit in accordance with the
disclosure.

FIG. 4 is a sectional view showing the obturation device
of the fluid circulation circuit in accordance with the dis-
closure, in the closed position.

FIG. 5 is a perspective view showing the piston of the
obturation device of the fluid circulation circuit in accor-
dance with the disclosure.

FIG. 6 is a perspective view showing the obturation
device of the fluid circulation circuit in accordance with the
disclosure, in the closed position.

FIG. 7 is a perspective view showing on one side the
obturation device of the fluid circulation circuit in accor-
dance with the disclosure, in the open position.

FIG. 8 is a perspective view showing on a side opposite
to the one illustrated in FIG. 7, the obturation device of the
fluid circulation circuit in accordance with the disclosure, in
the open position.

DETAILED DESCRIPTION

FIG. 1 illustrates by way of example, a medical endo-
scope 1 in a general sense designed to access the interior of
a body such as a cavity or a channel for example. Conven-
tionally, an endoscope 1 includes an insertion tube 2 having
on one side a proximal part $2_1$ connected to a control handle
3 and on the opposite side a distal part $2_2$ equipped with a
distal head 4. The insertion tube 2 is fixed temporarily or
permanently on the control handle 3. This insertion tube 2
which has a more or less significant length and flexibility is
intended to be introduced into a natural or artificial access
path with a view to performing various operations or func-
tions for therapeutic, surgical or diagnostic purposes. The
insertion tube 2 is made of a semi-rigid material and has a
length adapted to the length of the conduit to be inspected
and which can be comprised between 5 cm and 2 m. The
insertion tube 2 has various cross-sectional shapes such as
square, oval or circular shapes. This insertion tube 2 which
is in contact with the tissues, the human organs or medical
devices (trocars or probes), is essentially for single or
multiple use for a patient or is even reusable after decon-
tamination, disinfection or sterilization.

Conventionally, the endoscope 1 in accordance with the
disclosure includes a vision system V able to illuminate and
bring back an image of the distal part of the insertion tube
2, to an outer visualization system. The endoscope 1 thus
includes a vision system mounted inside the distal head 4,
with optical fibers bringing light and bringing back the
image, which will exit from the control handle 3, via the
proximal side of the control handle. In other cases, a CCD
(Charge Coupled Device) type camera is in the distal part,
mounted behind a prism, associated with an optical fiber for the light. The optical fiber and the video cable of the camera will exit through the control handle 3 on the proximal side of the control handle (FIG. 2).

Conventionally, the endoscope 1 also includes a control mechanism 5 that allows orienting the distal head 4 with respect to the longitudinal axis X of the insertion tube 2. This control mechanism 5 is not described in more detail because it is well known to those skilled in the art and is not specifically part of the disclosure.

As shown more specifically in FIG. 2, the endoscope 1 includes at least one fluid circulation circuit 10 intended to supply at least one fluid to the distal head 4 or to aspirate at least one fluid from the distal head. This circulation circuit 10 is equipped with at least one obturation device 11 that allows either opening or closing the circulation circuit 10. This obturation device 11 is mounted in the circulation circuit 10 to delimit on one side a first portion 10₁ called for example upstream portion and on another side a second portion 10₂ of the circulation circuit called downstream portion. This obturation device 11 which is manually controlled by an actuation button 12, is mounted inside the control handle 3, with the actuation button 12 which protrudes from the control handle to be accessible to an operator.

In the exemplary embodiment illustrated in the drawings, the first portion 10₁ of the circulation circuit 10 includes an inner segment mounted inside the control handle 3 mounted between the obturation device 11 and an endpiece 13 for connection to a fluid aspiration or supply source mounted at the proximal part of the control handle 3. The first portion 10₁ of the circulation circuit 10 also includes a tubular conduit, not represented in the drawings, mounted between the endpiece 13 and a fluid aspiration or supply source.

The second portion 10₂ of the circulation circuit includes an inner segment mounted inside the control handle 3 between the obturation device 11 and a first branch of a "Y"—shaped connector 14 mounted at the distal part of the control handle 3. This connector 14 includes a second branch 15 serving for the passage of various tools intended to be brought to the distal head 4 of the insertion tube 2. This second branch 15 of the connector is optionally closed by a plug 16. This connector 14 is provided with a common outlet intended to be provided with a tubular conduit 10b extending inside the insertion tube 2 up to its distal head 4. The second portion 10₂ of the circulation circuit thus extends outside the control handle, through this tubular conduit 10b.

As more specifically shown in FIGS. 3 and 4, the obturation device 11 of the circulation circuit 10 includes a piston body 17 in which a piston 18 is slidably guided along a direction of translation X. The body piston 17 has a generally tubular shape having, on the one hand, an open proximal end 17a beyond which the actuation button 12 protrudes and, on the other hand, a distal end 17d forming a bottom. This piston body 17 is fixed to the control handle 3. More specifically, the piston body 17 is fixed inside the control handle 3, for example, using an interlocking fixing system. The piston body 17 is externally provided, on either side, with two tubular shanks 19 intended to interlock into studs arranged inside the control handle 3.

The piston body 17 is externally equipped with a first tubing 21 for connection to the first portion 10₁ of the circulation circuit and a second tubing 22 for connection to the second portion 10₂ of the circulation circuit. As shown more specifically in FIGS. 2, 7, 8, the first tubing 21 and the second tubing 22 extend on either side of the piston body 17 along a common plane. As shown in the drawings, the first tubing 21 and the second tubing 22 are offset from each other along the direction of translation X of the piston 18. In the example illustrated, the second tubing 22 is closer to the actuation button 12 than the first tubing 21. As shown in the figures, the first tubing 21 and the second tubing 22 open out inside the piston body 17 via circular-shaped inlet sections 21a, 22a respectively. The inlet sections 21a, 22a for connection to the first portion 10₁ and to the second portion 10₂ of the circulation circuit are thus delimited respectively by the first tubing 21 and the second tubing 22.

According to one exemplary embodiment which appears more specifically in FIG. 4, the first tubing 21 and the second tubing 22 are externally provided with an anchoring system for the portions 10₁, 10₂ of the circulation circuit. As an anchoring system, each tubing 21, 22 is provided, for example, with a barb or a tailstock 23 ensuring permanent fixing of the portions of the circulation circuit on the tubing. According to one advantageous embodiment characteristic, the piston body 17 is externally equipped with fins 24 for guiding the actuation cables C of the deflection part.

The piston 18 is movably mounted in displacement in the piston body 17 between a closed position of the circulation circuit 10 illustrated in FIGS. 3, 4, 6 and an open position of the circulation circuit 10 illustrated in FIGS. 7 and 8. In the exemplary embodiment illustrated in the drawings, the piston 18 is guided in translation by means of a stud 25 carried by the piston 18 and engaged in a groove 26 arranged in the piston body 17 along a direction parallel to the direction of translation X (FIG. 3). The groove 26 opens out at the proximal end 17a of the piston body 17, in a slot 27 of smaller width than the width of the stud 25 to delimit an abutment 28 for the stud 25 corresponding to the closed position of the circulation circuit 10. This slot 27 ensures the passage, by deformation of the piston body 17, of the stud 25 so that the latter cooperates with the groove 26 allowing the assembly of the piston in the piston body.

According to one advantageous embodiment characteristic, the piston 18 is urged by an elastic return member 29 such as a helical compression spring, to automatically return to its closed position. The elastic return member 29 is mounted between the piston 18 and the bottom 17d of the piston body 17. Following an abutment on the actuation button 12, the elastic return member 29 is compressed by the piston until it occupies the open position. The elastic return member 29 allows automatically returning the piston 18 to its closed position.

According to an advantageous embodiment characteristic, the elastic return member 29 does not urge the piston to its closed position. In other words, when the piston 18 occupies its closed position of the circulation circuit 10, the stud 25 carried by the piston 18 cooperates with the abutment 28 with practically zero application force.

The piston 18 has on one side a part 18p called proximal part cooperating in a sealed manner with the piston body 17 to delimit, up to the proximal end 17a of the piston body, a mounting chamber 30 and on the opposite side a distal part 18d cooperating in a sealed manner with the piston body 17 to delimit, up to the bottom 17d of the piston body, an expansion chamber 31. The proximal part 18p of the piston 18 is provided with a seal 33 called proximal seal cooperating with the piston body 17 to ensure the sealing at the proximal part 18p of the piston. Similarly, the distal part 18d of the piston 18 is provided with a seal 34 called distal seal cooperating with the piston body 17 to ensure the sealing at the distal part of the piston.

The sealed proximal part 18p of the piston is extended by a head 18a extending inside the piston body and to the outside of the piston body 17, to be provided at its terminal part, with the actuation button 12. The sealed proximal part 18*p* of the piston delimits up to the proximal end 17*a* of the piston body, the mounting chamber 30 for the head 18*a* of the piston. This mounting chamber 30 therefore extends from the proximal seal 33 up to the proximal end 17*a* of the piston body.

According to an aspect of the disclosure, this mounting chamber 30 delimited between the piston 18 and the piston body 17 and between the proximal end 17*a* of the piston body and the sealed proximal part 18*p* of the piston communicates with the exterior of the piston body 17. As shown more specifically in FIG. 5, the head 18*a* of the piston is provided with openings 36 opening into the mounting chamber 30. Thus, the mounting chamber 30 communicates with the exterior of the piston body so that it can be properly sterilized.

The distal part 18*d* of the piston 18 cooperates in a sealed manner with the piston body 17 to delimit up to the bottom of the piston body, the expansion chamber 31. This expansion chamber 31 therefore extends from the distal seal 34 up to the bottom 17*d* of the piston body. This expansion chamber 31 communicates with an outlet vent 38 arranged in the bottom 17*d* of the piston body. Thus, the expansion chamber 31 communicates with the exterior of the piston body so that it can be properly sterilized.

According to another aspect of the disclosure, the piston 18 delimits with the piston body 17, a sealed interconnection chamber 40 adapted so that, in the open position of the obturation device 11 (FIGS. 7, 8), the sealed interconnection chamber 40 ensures the communication between the first portion 10₁ of the circulation circuit and the second portion 10₂ of the circulation circuit.

According to another aspect of the disclosure, the piston 18 delimits with the piston body 17, a sealed obturation section 42 so that in the closed position of the obturation device (FIGS. 4, 6), the sealed obturation section 42 closes a portion of the circulation circuit 10 while the sealed interconnection chamber 40 communicates with another portion of the circulation circuit 10. In the exemplary embodiment illustrated in the drawings, the sealed obturation section 42 closes the first portion 10₁ of the circulation circuit 10 while the sealed interconnection chamber 40 communicates with the second portion 10₂ of the circulation circuit 10. Thus, the sealed obturation section 42 closes the first tubing 21 that is to say the inlet section 21*a* and the sealed interconnection chamber 40 communicates with the second tubing 22, namely the inlet section 22*a*.

According to an advantageous embodiment characteristic, the sealed interconnection chamber 40 includes a hole 45 arranged to pass right through the piston 18 and open out into a cylindrical chamber 46 delimited between the piston 18 and the piston body 17. As shown in FIGS. 7 and 8, the hole 45 has an oblong section so as to be located in the open position of the circulation circuit, facing or opposite the tubing 21, 22 to limit the pressure drop. Thus, in the open position of the circulation circuit, the inlet section 21*a* of the first tubing 21 is located facing or opposite the hole 45 and the inlet section 22*a* of the second tubing 22 is also located facing or opposite the hole 45. Thus, the inlet sections 22*a*, 22*b* of the tubing 21, 22 open out without section reduction, in the cylindrical chamber 46 and the hole 45. The positioning of the hole 45 facing the inlet sections 22*a*, 22*b* of the tubing 21, 22 is advantageously ensured by the translation guidance of the piston 18.

The sealed interconnection chamber 40 thus ensures communication between the first portion 10₁ of the circulation circuit and the second portion 10₂ of the circulation circuit, without restriction of the fluid passage section between the inlet sections 22*a*, 22*b* of the first and second tubing 21, 22. It follows that the obturation device 11 of the circulation circuit causes no pressure drop for the circulation of the fluid.

The sealing of the sealed interconnection chamber 40 is ensured by seals 33, 49 carried by the piston 18 and disposed on either side of the cylindrical chamber 46 and of the hole 45. In the exemplary embodiment illustrated in the drawings, the seal 33 called proximal seal ensures the sealing on one side of the sealed interconnection chamber 40 while the sealing on the other side of the sealed interconnection chamber 40 is ensured by a seal 49 called intermediate seal carried by the piston 18.

According to this advantageous alternative embodiment, the proximal seal 33 ensures the sealing of the sealed interconnection chamber 40 and the mounting chamber 30. Of course, an alternative embodiment can be envisaged, implementing two seals placed in the vicinity of each other so that each of them ensures the sealing of a chamber.

The sealed obturation section 42 is dimensioned to close, in the example illustrated, the first portion 10₁ of the circulation circuit 10, that is to say the first tubing 21 when the piston 18 occupies its closed position. To this end, the piston 18 is provided with two seals cooperating with the piston body, on either side of the first tubing 21. According to one preferred exemplary embodiment illustrated in the drawings, the sealing of the sealed obturation section 42 is ensured on the one hand, by the distal seal 34 carried by the distal part of the piston and on the other hand, advantageously by the seal 49 called intermediate seal. Of course, the sealing of the sealed obturation section 42 can be ensured by additional seals different from the distal seal 34 and from the intermediate seal 49. According to the preferred alternative embodiment, the seal 49 called intermediate seal ensures the sealing between the sealed interconnection chamber 40 and the sealed obturation section 42. Thus, the sealing between the mounting chamber 30 and the sealed interconnection chamber 40, between the sealed interconnection chamber 42 and the sealed obturation section 42, and between the sealed obturation section 42 and the expansion chamber 31 are ensured by means of three seals respectively 33, 49, 34 advantageously produced by O-rings. For example, these seals can be added or overmolded on the piston 18.

It appears from the foregoing description that the object of the disclosure proposes an endoscope having a fluid circulation circuit 10 integrating an obturation device 11 and which can be sterilized in a safe and complete manner. Indeed, in the closed position, all the inner parts of the obturation device 11 can be sterilized since they are in communication with the exterior of the obturation device. Thus, can be sterilized:

the inner volume delimited inside the piston body 17 up to the proximal seal 33 and corresponding to the mounting chamber 30;

the first part of the second portion 10₂ of the circulation circuit extending up to the sealed interconnection chamber 40, via the second tubing 22;

the first part of the first portion 10₁ opening out at the proximal part of the control handle 3, and extending up to the sealed obturation section 42, via the first tubing 21;

the inner volume delimited inside the piston body 17 up to the distal seal 34 and corresponding to the expansion chamber 31.

In the exemplary embodiment illustrated in the drawings, the sealed interconnection chamber 40 is arranged in the proximal part of the piston while the sealed obturation section 42 is arranged in the distal part of the piston. Of course, the positions between the sealed interconnection chamber 40 and the sealed obturation section 42 can be reversed. Thus, the proximal seal 33 ensures the sealing between, on the one hand, the mounting chamber 30 and, on the other hand, the sealed interconnection chamber 40 or the sealed obturation section 42 according to the inverted alternative not represented. Similarly, the distal seal 34 ensures the sealing between, on the one hand, the expansion chamber 31 and, on the other hand, the sealed obturation section 42 or the sealed interconnection chamber 40 according to the inverted alternative not represented.

The disclosure is not limited to the examples described and represented because various modifications can be made thereto without departing from its scope.

The invention claimed is:

1. A medical endoscope including an insertion tube connected at an insertion tube proximal part to a control handle and provided at an insertion tube distal part with a distal head, the medical endoscope including at least one fluid circulation circuit in which an obturation device of the at least one fluid circulation circuit is mounted including:

a piston body fixed to the control handle and in which a piston is movably mounted in displacement between a closed position of the at least one fluid circulation circuit and an open position of the at least one fluid circulation circuit;

the piston body comprising a sealed obturation section and a sealed interconnection chamber located between the piston and the piston body;

wherein in the open position, the sealed interconnection chamber ensures communication between a first portion of the at least one fluid circulation circuit and a second portion of the at least one fluid circulation circuit;

wherein in the closed position, the sealed interconnection chamber communicates with the second portion of the at least one fluid circulation circuit while the sealed obturation section closes the first portion of the at least one fluid circulation circuit;

the piston including, a piston proximal part cooperating in a sealed manner with the piston body and extending outside the piston body, by a button for actuating the piston, and the piston comprising a piston distal part cooperating in a sealed manner with the piston body to delimit up to a bottom of the piston body;

an expansion chamber communicating with an outlet vent arranged in the bottom of the piston body;

the piston proximal part cooperating in a sealed manner with the piston body delimiting up to a proximal end of the piston body;

a mounting chamber for a head of the piston communicating with an exterior of the piston body;

the sealed interconnection chamber including a hole passing right through the piston to open out into a cylindrical chamber delimited between the piston and the piston body, by an oblong section located in the open position of the at least one fluid circulation circuit, facing inlet sections for connection to the first portion and to the second portion of the at least one fluid circulation circuit to limit a pressure drop; and wherein an elastic compression return member is mounted in a compression chamber between the piston distal part and the bottom of the piston body to urge the piston to automatically return the piston to the closed position.

2. The medical endoscope of claim 1, wherein the piston is slidably guided along a direction of translation in the piston body.

3. The medical endoscope of claim 1, wherein the elastic compression return member is mounted between the piston and the bottom of the piston body so as not to urge the piston into the closed position.

4. The medical endoscope of claim 1, wherein the piston proximal part is provided with a proximal seal ensuring sealing between the mounting chamber and the sealed interconnection chamber or the sealed obturation section.

5. The medical endoscope of claim 1, wherein the piston distal part is provided with a distal seal ensuring sealing between the expansion chamber and the sealed obturation section or the sealed interconnection chamber.

6. The medical endoscope of claim 1, wherein the sealed obturation section of the piston is delimited on one side by a distal or proximal seal and on the opposite side by an intermediate seal ensuring sealing between the sealed interconnection chamber and the sealed obturation section.

7. The medical endoscope of claim 1, wherein the piston body is equipped with a first tubing for connection to the first portion of the at least one fluid circulation circuit and with a second tubing for connection to the second portion of the at least one fluid circulation circuit, the first tubing and the second tubing extending on either side of the piston body along a common plane.

8. The medical endoscope of claim 1, wherein the inlet sections for connection to the first portion and to the second portion of the at least one fluid circulation circuit are delimited respectively by a first tubing and a second tubing offset from each other along the direction of displacement of the piston.

9. The medical endoscope of claim 7 or 8, wherein the first tubing and the second tubing are externally provided with an anchoring system for the portions of the at least one fluid circulation circuit.

10. The medical endoscope of claim 1, wherein the piston body is provided with an interlocking fixing system inside the control handle.

11. The medical endoscope of claim 1, wherein the piston body is externally equipped with fins for guiding actuation cables to orient the distal head.

\* \* \* \* \*